(12) United States Patent
Withers

(10) Patent No.: US 9,051,085 B2
(45) Date of Patent: Jun. 9, 2015

(54) CONTAINER WITH AIR FRESHENER

(75) Inventor: Philip Craig Withers, South Bank (AU)

(73) Assignee: Intellectual Property Development Corporation Pty Ltd, Melbourne (AU)

( * ) Notice: Subject to any disclaimer, the term of this patent is extended or adjusted under 35 U.S.C. 154(b) by 1074 days.

(21) Appl. No.: 12/825,739

(22) Filed: Jun. 29, 2010

(65) Prior Publication Data

US 2011/0000977 A1 Jan. 6, 2011

Related U.S. Application Data

(60) Provisional application No. 61/221,738, filed on Jun. 30, 2009.

(51) Int. Cl.
*A61L 9/04* (2006.01)
*A61L 9/12* (2006.01)
*B65D 23/12* (2006.01)
*B65D 25/20* (2006.01)

(52) U.S. Cl.
CPC ............ *B65D 25/20* (2013.01); *A61L 2209/13* (2013.01)

(58) Field of Classification Search
CPC ............ A61L 9/04; A61L 9/048; A61L 9/12; A61L 2209/13; A61L 2209/133; A61L 2209/135; B05B 11/0005; B05B 11/0037; A01M 1/2055; B65D 23/12; B65D 25/20
USPC .................... 239/6, 34, 54–60, 289; 222/192; 206/216, 223, 527, 581; 215/6, 228, 215/386, 390, 395

See application file for complete search history.

(56) References Cited

U.S. PATENT DOCUMENTS

| | | | | |
|---|---|---|---|---|
| 5,353,546 | A * | 10/1994 | Bock | 47/66.6 |
| 5,799,826 | A * | 9/1998 | Brown et al. | 222/4 |
| 6,569,387 | B1 * | 5/2003 | Furner et al. | 239/289 |
| 6,769,631 | B2 * | 8/2004 | Brown | 239/289 |
| 7,137,534 | B2 * | 11/2006 | Patel | 222/192 |
| 7,284,711 | B2 * | 10/2007 | Reed et al. | 239/59 |
| 8,302,819 | B2 * | 11/2012 | Dente et al. | 222/173 |
| 2006/0000921 | A1 * | 1/2006 | Quintard et al. | 239/44 |
| 2006/0283888 | A1 * | 12/2006 | Kinscherf et al. | 222/192 |
| 2008/0245889 | A1 * | 10/2008 | Klabbers et al. | 239/55 |

FOREIGN PATENT DOCUMENTS

WO    WO 2005068308 A1 *  7/2005  ............... B65D 6/00

* cited by examiner

*Primary Examiner* — Darren W Gorman
(74) *Attorney, Agent, or Firm* — K&L Gates LLP

(57) ABSTRACT

A container for dispensing a pourable composition and an air freshener, the container comprising: a container body for the pourable composition, and an air freshening unit attached or attachable to a lower periphery of the container body, and comprising a housing and a closure. The closure closes an aperture in the housing through which the air freshener is loadable into the air freshener unit and thereby retains the air freshener in the air freshener unit, and the closure and the air freshener housing are mutually engageable.

2 Claims, 7 Drawing Sheets

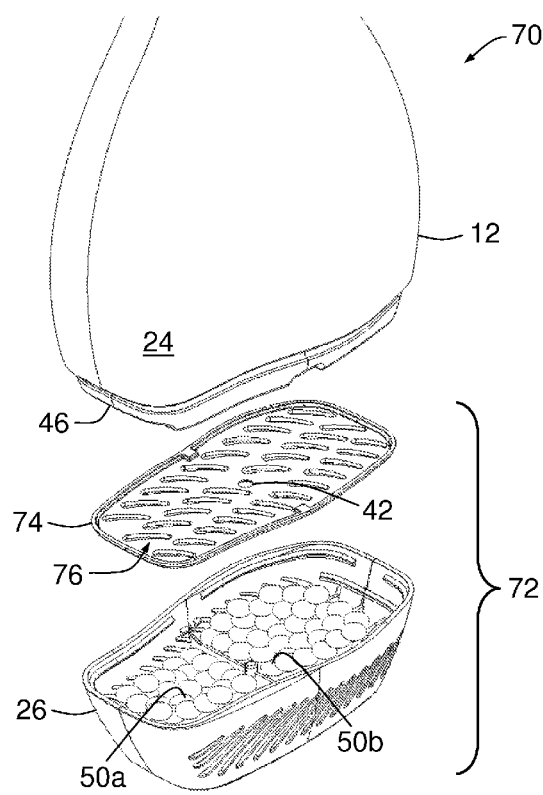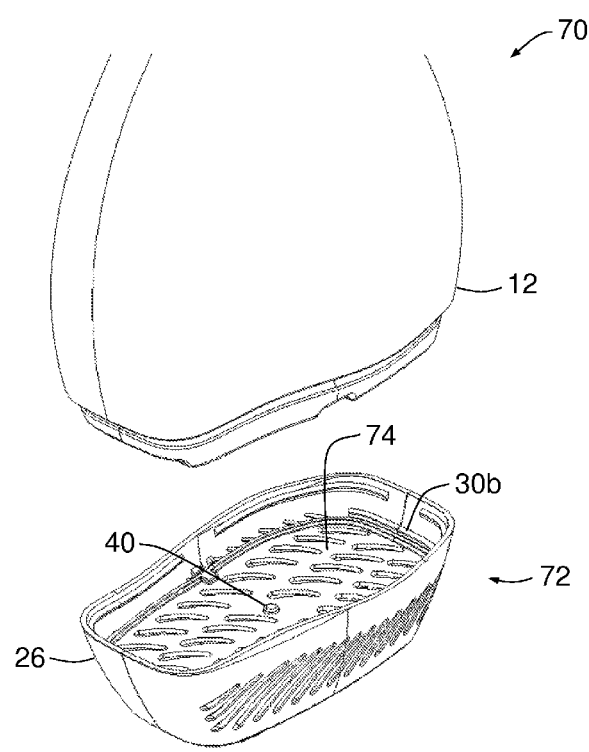
Figure 9
Figure 10

CONTAINER WITH AIR FRESHENER

RELATED APPLICATION

This application is based on and claims the benefit of the filing date of U.S. application No. 61/221,738 filed 30 Jun. 2009, the content of which as filed is incorporated herein by reference in its entirety.

FIELD OF THE INVENTION

The present invention relates to a container for dispensing a pourable composition and an air freshener, of particular but by no means exclusive application for containing skin moisturizer or detergent as well as the air freshener.

BACKGROUND OF THE INVENTION

WO 2007/113774 (Procter & Gamble) discloses a combined dispensing container and air freshener comprising a container body for containing detergent to be dispensed and an air freshening unit permanently attached to the container body with a fixed volume of greater than 45 mL. A number of examples of suitable air fresheners are disclosed, including air fresheners in the form of polymeric particles comprise foamed or non-foamed low density polyethylene, high density polyethylene, polypropylene, the copolymer of ethylene and vinyl acetate and polyvinyl chloride. The particles are said to be preferably substantially spherical. The air freshener, comprising spherical particles or otherwise, is retained within a volume defined by the side walls and base of an air freshening unit and the base of the container body. It appears that the air freshener is inserted into the air freshening unit before the air freshening unit is attached to the container body, and retained in the air freshening unit by the attachment of the container body to the air freshening unit.

SUMMARY OF THE INVENTION

According to a first broad aspect of the present invention, therefore, there is provided a container for dispensing a pourable composition and an air freshener, the container comprising:

a container body for the pourable composition; and an air freshening unit attached or attachable to a lower periphery of the container body, and comprising a housing and a closure;

wherein the closure closes an aperture in the housing through which the air freshener is loadable into the air freshener unit and thereby retains the air freshener in the air freshener unit, and the closure and the air freshener housing are mutually engageable.

In some embodiments, the container includes the pourable composition and/or the air freshener.

In one embodiment, the air freshening unit is adapted to receive and contain air freshener in the form of one or more solids or gels, or a mixture of one or more solids and gels.

In a particular embodiment, the air freshening unit is adapted to receive and contain air freshener in the form of beads (of any desired shape) of air freshening material.

The air freshener may be of any suitable composition. In one embodiment, the air freshening unit is adapted for use with an air freshener initially comprising at least 15%, preferably at least 20% and more preferably at least 25% fragrance by weight.

In one embodiment, the housing of the air freshening unit has one or more vents for emitting fragrance from the air freshener. Preferably, each of the vents has a large venting area and is shaped to retain the air freshener.

The closure may have one or more vents for emitting fragrance from the air freshener.

In embodiments with vents in both housing and closure, ventilation of fragrance is improved owing to air flow (even if low) through the closure, air freshener and housing in turn (or vice versa).

In one embodiment, the housing and the closure are engageable in a manner that inhibits manual removal of the closure from the air freshener housing, and in one embodiment in a manner that prevents manual removal of the closure.

In one particular embodiment, the closure is a child-resistant closure.

Thus, whereas in the prior art it is seemed unnecessary to include a closure or comparable element owing to the retention of the air freshening unit with the container body, according to the present invention a closure is employed so that the air freshener can be loaded into the air freshening unit and retained therein securely before the container body is attached. This is of particular value where the container body and air freshening unit are manufactured or transported separately. In addition, the closure inhibits the spilling or loss of air freshener should the container body and air freshening unit become separated.

The latter is particularly important in retail environments, where the spilling of—for example—beads of air freshener can present a safety hazard. In addition, the closure inhibits access by children to the air freshener should the container body and air freshening unit become separated in, for example, a domestic environment. This is an important safety consideration, as some air freshening compositions are hazardous if ingested.

In one embodiment, the closure is affixed to the housing, such as with glue, spot welding, a mechanical mechanism or otherwise.

In one particular embodiment, the housing has a flange or flanges for retaining the closure. In this embodiment, the housing may have an abutment (such as in the form of a buttress or buttresses), and the closure is adapted to be located and retained between the flange or flanges and the abutment.

In one embodiment, the housing includes one or more walls that divide the housing into a plurality of compartments.

Thus, in this embodiment, separate air fresheners of air freshening compositions may be located in each of the respective compartments.

According to a second broad aspect of the present invention, there is provided a method for assembling a container for dispensing a pourable composition and an air freshener, comprising:

loading the air freshener into an air freshening unit;

closing said air freshening unit with a closure; and engaging said air freshening unit with a container body adapted to contain the pourable composition.

It will be understood by the skilled person that the closure need not seal the air freshening unit but rather "close" the unit against the accidental loss of air freshening composition, at least the time of manufacture of the container.

The method may also include fastening a removeable cover over vents in the air freshening unit.

Thus, in use the removable cover is removed by the user, so that air freshener may be released.

According to a third broad aspect of the present invention, there is provided an air freshening unit for use in a container for dispensing a pourable composition and an air freshener, the air freshening unit comprising:

an air freshening unit attached or attachable to a lower periphery of a container body of the container, and comprising a housing and a closure;

wherein the closure closes an aperture in the housing through which the air freshener is loadable into the air freshener unit and thereby retains the air freshener in the air freshener unit, and the closure and the air freshener housing are mutually engageable.

Thus, the air freshening unit also embodies the present invention.

According to a fourth broad aspect of the present invention, there is provided a method of retaining air freshener in a container for dispensing a pourable composition and air freshener, comprising:

loading the air freshener into an air freshening unit;
closing said air freshening unit with a closure; and
engaging said air freshening unit with a container body of the container, the container body being adapted to contain the pourable composition.

It should be noted that each of the various features of each of the above aspects of the invention can be combined or provided in the other aspects as suitable and desired.

BRIEF DESCRIPTION OF THE DRAWINGS

In order that the invention may be more clearly ascertained, embodiments will now be described, by way of example, with reference to the accompanying drawings, in which:

FIG. 9 is a partial exploded view of the container of FIG. 8, with air freshener (comparable to FIG. 3); and FIG. 10 is a partial exploded view of the container of FIG. 8, with air freshening unit closed (comparable to FIG. 4).

DETAILED DESCRIPTION OF THE EMBODIMENT

Figure 1:
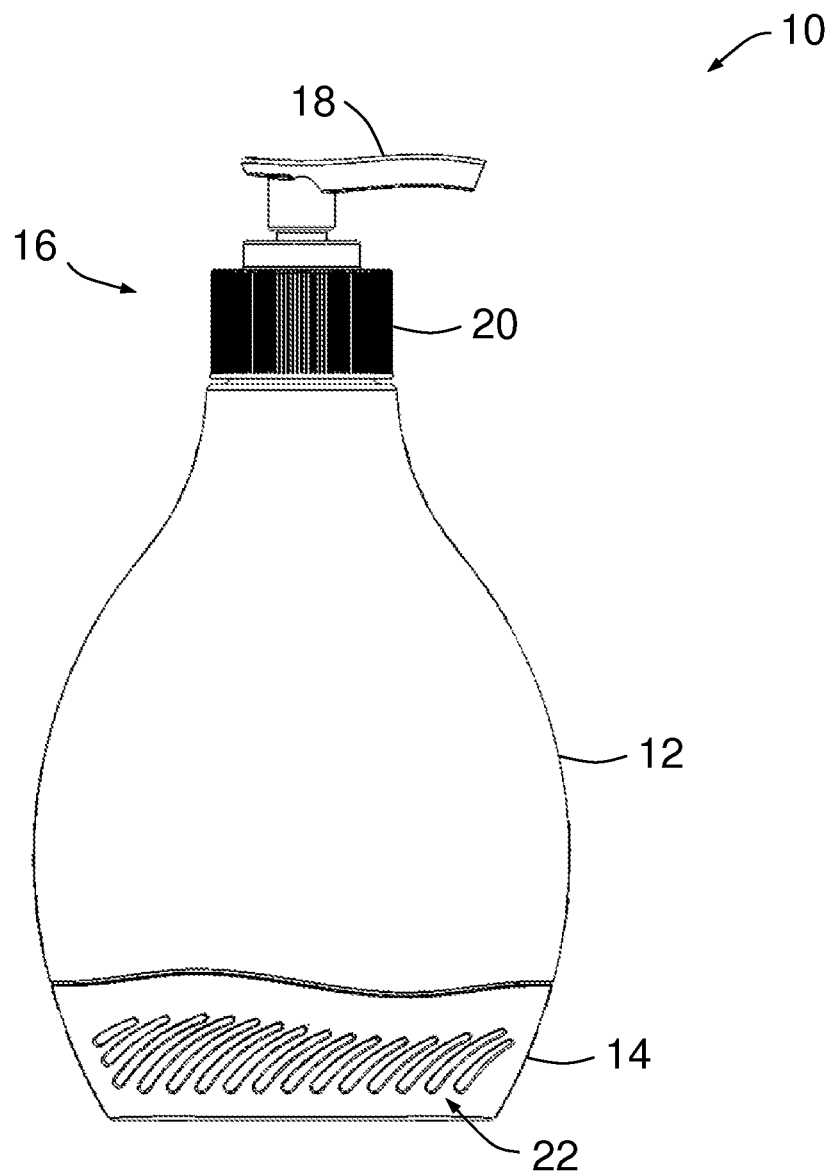
FIG. 1 is a view of a combined skin moisturizer and air freshener container according to an embodiment of the present invention.

A combined skin moisturizer and air freshener container according to an embodiment of the present invention is shown at 10 in FIG. 1. Container 10 is of a plastics material, but may be of any suitable material including one or more plastics materials, ceramics or glass, and—if of plastics materials—may be blow- or injection-molded. Suitable plastics materials include polypropylene and polyesters. The overall height of container 10 is 169 mm, but it will be appreciated that the size of container 10 may be varied as desired.

Container 10 comprises a container body 12 and an air freshening unit 14. Container 10 also includes a dispensing unit 16 comprising a pump-action dispensing nozzle 18 and a cap 20; dispensing unit 16 is threadedly attached to container body 12 by cap 20, and thereby both closes container body 12 and allows the dispensing of skin moisturizer contained in container body 12.

Air freshening unit 14 contains air freshener (not shown) and is provided with a plurality of vents 22 on the front and rear faces of air freshening unit 14 to allow air freshener to be passively dispensed from air freshening unit 14. In this embodiment, vents 22 range in size from approximately 12×1.6 mm to approximately 21×1.8 mm.

The air freshener may be in any form that is retainable notwithstanding the provision of vents 22, such as in solid or gel form and, similarly, in any desired shape (though it is envisaged that the air freshener will typically comprise beads). In this embodiment, the air freshener comprises spherical or ellipsoidal beads comprising ethylene vinyl acetate (EVA) and a fragrance, from which the fragrance progressively dissipates to provide the air freshening action. The beads initially comprise 25% fragrance by weight. The fragrance may comprise natural essential oils, a mixture of fragrant ingredients or otherwise (as desired). As will be understood by those skilled in the art, a fragrance ingredient is any basic substance used in the manufacture of fragrance materials for its odorous, odour-enhancing, or blending properties, whether obtained by chemical synthesis from synthetic, fossil, or natural raw materials, or by physical operations from natural sources, and comprising aroma chemicals, essential oils, natural extracts, distillates and isolates, and oleoresins. In this embodiment the fragrance comprises a mixture of fragrant ingredients (including, for example, hexamethy lindanopyran or hexylsalicylate) dosed at 25% during the extrusion process by which the beads are manufactured.

The proportion of fragrance (25% by weight) is relatively high, but has the advantage that the air freshening action of the air freshener will be of a satisfactorily high level (for most users), bearing in mind that container 10 will often be stationary for extended periods so the beads may be only infrequently agitated. As will also be appreciated by those skilled in the art, periodic agitation of container 10—and hence of the air freshener beads—will generally release greater quantities of air freshening fragrance than when container 10 remains stationary.

Lower proportions of fragrance (such as at least 15% or at least 20% by weight) may be employed in other embodiments, as desired, to correspondingly lesser effect.

Figure 2:
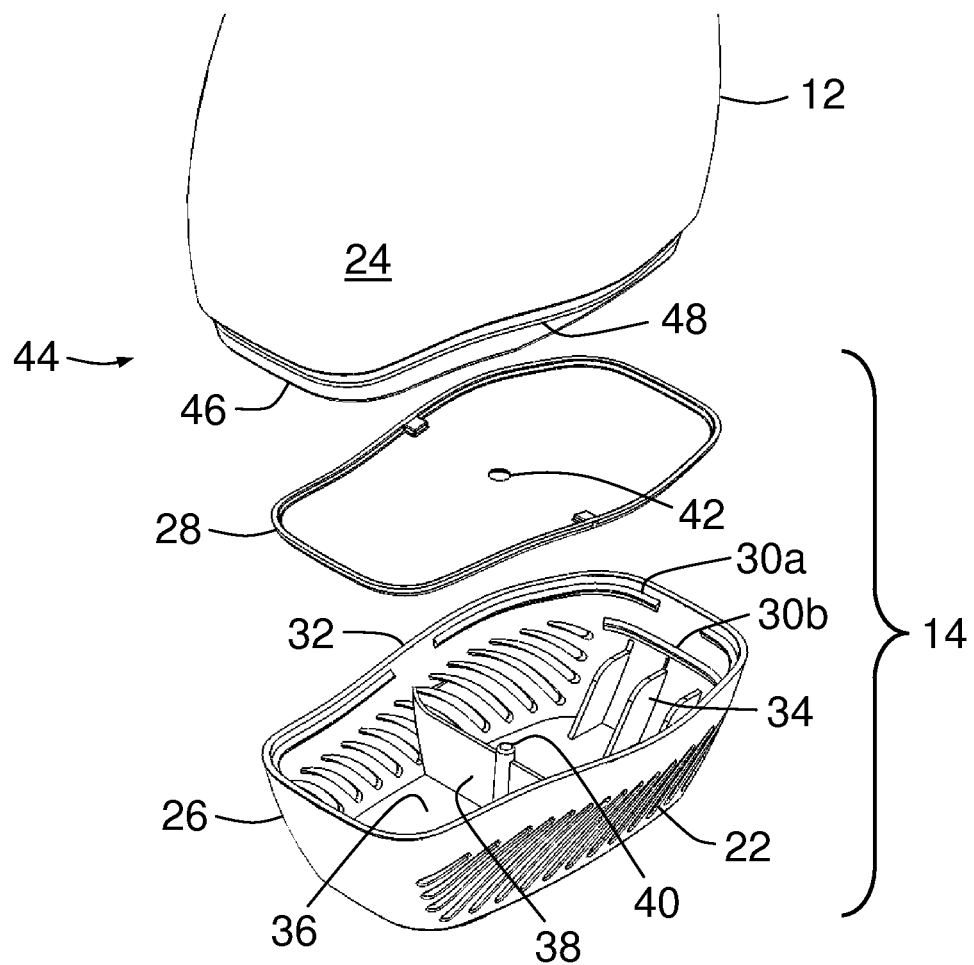
FIG. 2 is a partial exploded view of the container of FIG. 1, without air freshener.

FIG. 2 is a partial exploded view of container 10, showing the lower periphery 24 of container body 12 and air freshening unit 14. (It should be noted that the air freshener has been omitted for clarity.)

Air freshening unit 14 includes a housing 26 and a closure 28. Closure 28 is adapted to close housing 26 after air freshener has been loaded into housing 26, so that air freshener is not accidentally displaced from air freshening unit 14 either before air freshening unit 14 is attached to container body 12 or should air freshening unit 14 and container body 12 become detached.

Housing 26 has two flanges on its interior surface. The first flange 30a is immediately below an upper periphery 32 of housing 26, and is adapted to engage a corresponding groove (discussed below) in container body 12. Second flange 30b is in two portions, one at each end of the interior of housing 26, and is positioned below first flange 30a. Second flange 30b is adapted to retain closure 28. Housing 26 includes six buttresses 34, three at each end of housing 26, that extend from the floor 36 of housing 26 to a respective side wall of housing 26, and defining a stop position for closure 28. Thus, when closure 28 is inserted into housing 26, it must be forced past second flange 30b until it abuts buttresses 34, and is hence held securely in position between second flange 30b and buttresses 34. Closure 28 is manufactured to fit housing 26 precisely, so that it cannot be removed manually by a user.

Housing 26 also includes a central, dividing wall 38 that partitions air freshening unit 14 into two portions, so that two different air freshening compositions can be contained in air freshening unit 14 but kept separate. Central wall 38 has a centrally located, upwardly extending post 40 that is received by a corresponding aperture 42 in closure 28 once air freshening unit 14 has been assembled. Optionally, post 40 and closure 28 may be adapted to lock together. For example, post 40 may be formed—at its upper end—into an upwardly directed arrow head or set of downwardly directed barbs that is passed through aperture 42 during manufacture or assembly and adapted to resist subsequent removal.

Wall 38 additionally inhibits the removal of closure 28, as it prevents the downward distortion of closure 28 that might otherwise be used to facilitate its removal. Post 40 inhibits any tendency of wall 38 to be bent downwards upon the application of such downward pressure to closure 28.

As is apparent in FIG. 2, the lower periphery 44 of container body 12 has an inward step 46 that is received by housing 26 of air freshening unit 14. Step 46 is provided with a continuous groove 48 that receives first flange 30a of housing 26, thereby allowing container body 12 to securely engage air freshening unit 14.

Figure 3:
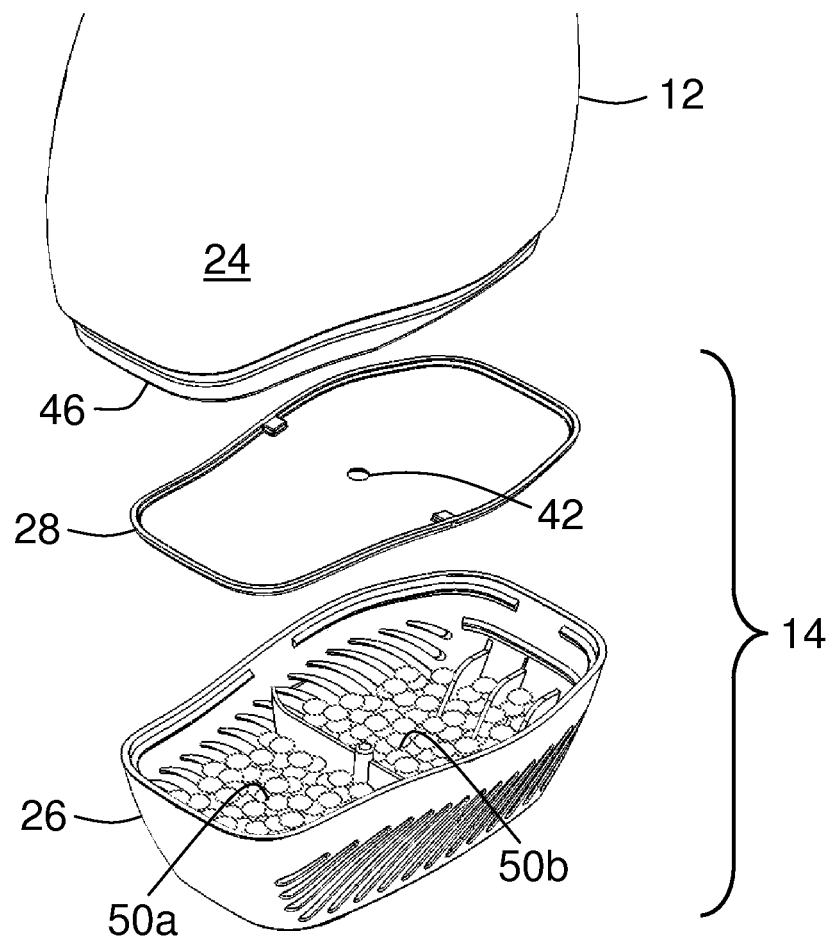
FIG. 3 is a partial exploded view of the container of FIG. 1, with air freshener.

FIG. 3 is comparable to the partial exploded view of FIG. 2, but showing beads 50a, 50b of air freshener. Beads 50a, 50b are of two colours: beads 50a are of a first colour and occupy a first compartment defined in housing 26 by wall 38, and are separated by wall 38 from beads 50b of a second colour occupying a second compartment defined in housing 26 by wall 38.

Figure 4:
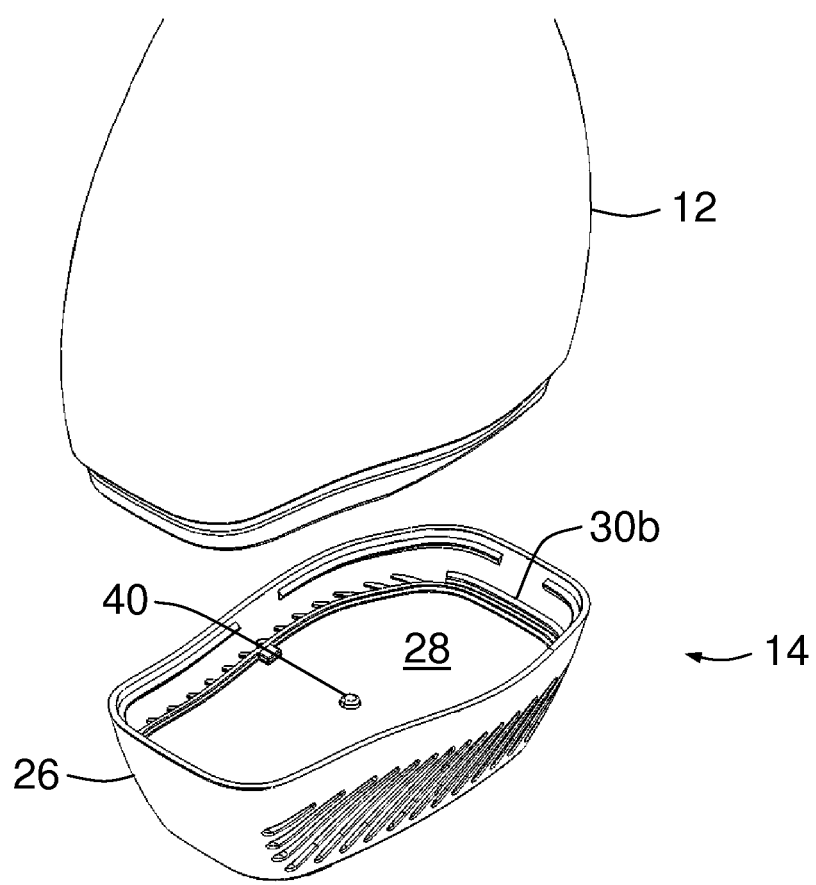
FIG. 4 is a partial exploded view of the container of FIG. 1, with air freshening unit closed.

FIG. 4 is comparable to the partial exploded views of FIGS. 2 and 3, but shows closure 28 and housing 26 engaged. As is apparent in this view, closure 28 is retained within housing 26 by second flange 30b.

Figure 5:
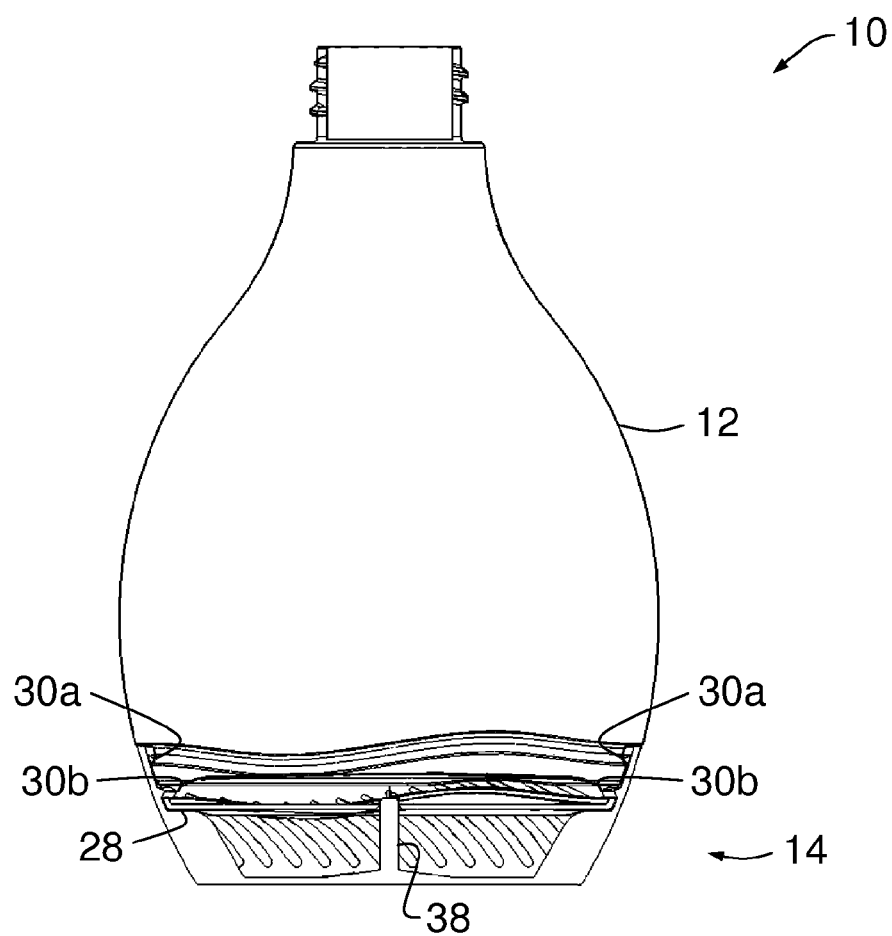
FIG. 5 is a cross sectional view of the container of FIG. 1, through a vertical plane.

FIG. 5 is a cross sectional view of container 10 (though dispensing unit 16 has been omitted for clarity). The engagement of closure 28 with second flange 30b is particularly apparent in this view.

Figure 6:
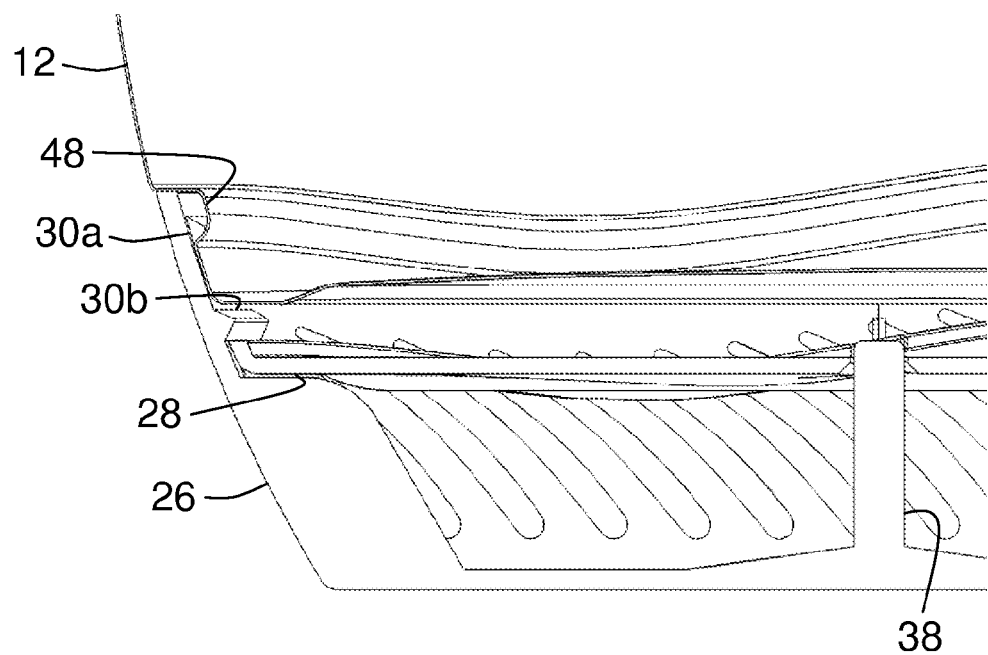
FIG. 6 is a detail of the view of FIG. 5.

FIG. 6 is a detail of FIG. 5, again showing the engagement of closure 28 with second flange 30b. Also apparent is the engagement of first flange 30a within groove 48.

Figure 7:
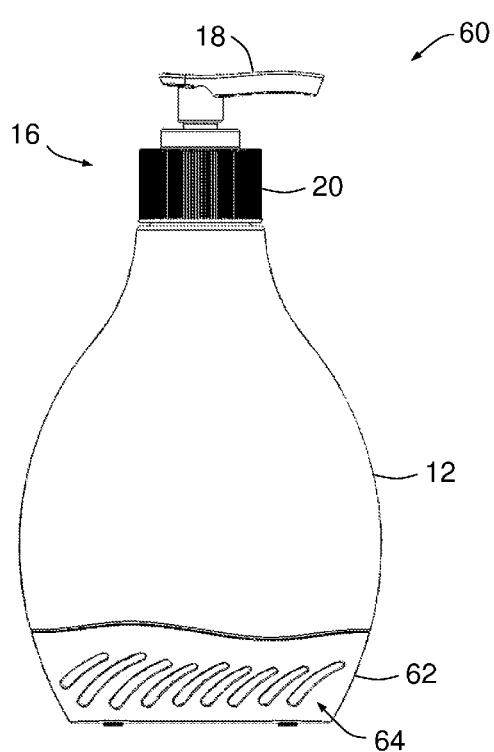
FIG. 7 is a view of a combined skin moisturizer and air freshener container according to a second embodiment of the present invention.

A combined skin moisturizer and air freshener container according to a second embodiment of the present invention is shown at 60 in FIG. 7. Container 60 is comparable in most respects to container 10 of FIG. 1, and like reference numerals have been used to indicate like features. Container 60 has an air freshening unit 62 (cf. air freshening unit 14 of container 10 of FIG. 1) with a plurality of vents 64 on its front and rear faces to allow air freshener to be passively dispensed, but vents 64 of air freshening unit 62 are significantly larger—that is, significantly larger venting area—than vents 22 of air freshening unit 14.

The larger venting area of vents 64 allows more rapid dispersal of fragrance, whose strength may otherwise be less than desired by some users. The air freshener beads of this embodiment, therefore, may be larger than in the embodiment of FIG. 1, so that they cannot fall out of vents 64.

Figure 8:
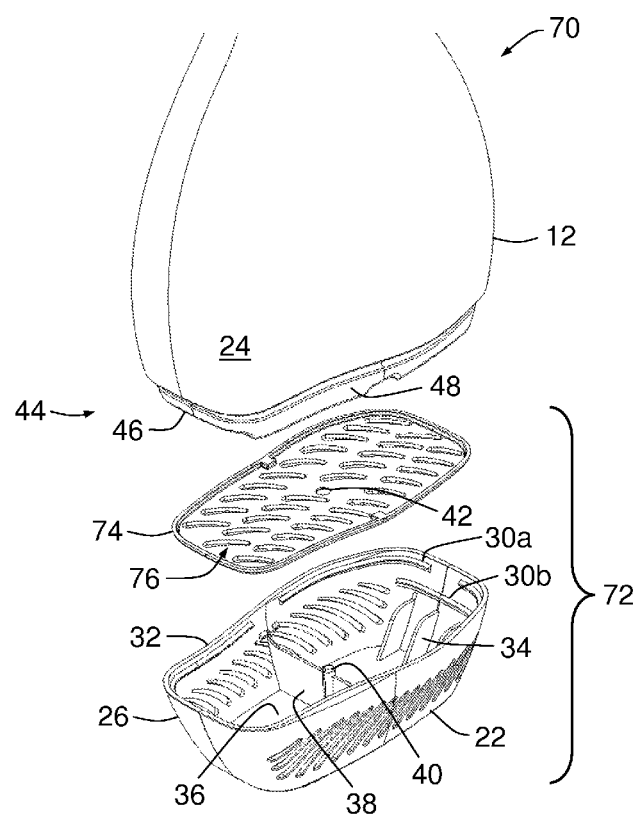
FIG. 8 is a partial exploded view of a combined skin moisturizer and air freshener container according to a third embodiment of the present invention (comparable to FIG. 2)

FIG. 8 is a partial exploded view of a combined skin moisturizer and air freshener container 70 according to a third embodiment of the present invention. Container 70 is comparable in most respects to container 10 of FIG. 1, and like reference numerals have been used to indicate like features. FIG. 8 omits the upper portion of container 70 (including a dispensing unit with a pump-action dispensing nozzle and a cap that is identical to dispensing unit 16 of container 10), and is comparable to the partial view of container 10 shown in FIG. 2.

Like container 10, container 70 includes a container body 12 and an air freshening unit 72. (The air freshener has been omitted for clarity in this view.) Air freshening unit 72 is generally identical with air freshening unit 14 of container 10, and includes a housing 26 and a closure 74. However, unlike closure 28 of container 10, closure 74 of container 70 has a plurality of vents 76 for emitting fragrance from the air freshener in air freshening unit 72. In this embodiment, therefore, vents are provided in both housing 26 and closure 74. Ventilation of fragrance is expected to be improved owing to air flow (even if low) through closure 74, air freshener and housing 26 in turn (or vice versa).

FIG. 9 is comparable to the partial exploded view of FIG. 8 (cf. FIG. 3), but showing beads 50a, 50b of air freshener in housing 26. FIG. 10 is comparable to the partial exploded views of FIGS. 8 and 9 (cf. FIG. 4), but shows closure 74 and housing 26 engaged. As is apparent in this view, closure 74 is retained within housing 26 by second flange 30b.

It will be appreciated that each of the features of the three embodiments described above may be combined as desired. For example, in another embodiment, the closure of the air freshening unit has vents (cf. FIG. 8) and the housing of the air freshening unit has larger vents (cf. FIG. 7).

Modifications within the scope of the invention may be readily effected by those skilled in the art. It is to be understood, therefore, that this invention is not limited to the particular embodiments described by way of example hereinabove.

In the preceding description of the invention and in the claims that follow, except where the context requires otherwise owing to express language or necessary implication, the word "comprise" or variations such as "comprises" or "comprising" is used in an inclusive sense, that is, to specify the presence of the stated features but not to preclude the presence or addition of further features in various embodiments of the invention.

Further, any reference herein to prior art is not intended to imply that such prior art forms or formed a part of the common general knowledge in any other country.

The claims defining the invention are as follows:

1. A combined dispensing container and air freshener housing, comprising:
   a dispensing container comprising a container body having a neck, side walls and a base, wherein a dispensing nozzle is removably attachable to the neck of the container body; and
   an air freshener housing comprising an upper opening, vented side walls, a base, and a lid, wherein upper portions of the vented side walls are removably attachable to the base of the container body, wherein the lid is lockably attachable to the air freshener housing via a barbed post-and-hole connection to close the upper opening, wherein the air freshener housing further comprises an internal wall between the side walls, and wherein the barbed post-and-hole connection comprises a barbed post on top of the internal wall and a hole through the lid.

2. The combined dispensing container and air freshener housing of claim 1, wherein the upper portions of the vented side walls comprise a peripheral flange and the base of the container body comprises a peripheral groove, and wherein the upper portions of the vented side walls are removably attachable to the base of the container body via engagement of the peripheral flange and the peripheral groove.

* * * * *